United States Patent
Mollov et al.

(10) Patent No.: US 10,682,116 B2
(45) Date of Patent: Jun. 16, 2020

(54) MISALIGNMENT COMPENSATION IN DUAL X-RAY IMAGER

(71) Applicant: VAREX IMAGING CORPORATION, Salt Lake City, UT (US)

(72) Inventors: Ivan Mollov, Mountain View, CA (US); Eric Amusin, Northbrook, IL (US); Arundhuti Ganguly, San Jose, CA (US)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 23 days.

(21) Appl. No.: 15/823,533

(22) Filed: Nov. 27, 2017

(65) Prior Publication Data

US 2019/0159749 A1 May 30, 2019

(51) Int. Cl.
  *A61B 6/00* (2006.01)
  *H01L 27/146* (2006.01)
  *G06T 1/00* (2006.01)
  *G06T 5/50* (2006.01)
  *G01T 1/20* (2006.01)

(52) U.S. Cl.
  CPC .......... *A61B 6/587* (2013.01); *A61B 6/4233* (2013.01); *A61B 6/58* (2013.01); *G01T 1/2018* (2013.01); *G06T 1/0007* (2013.01); *G06T 5/50* (2013.01); *H01L 27/14658* (2013.01); *H01L 27/14663* (2013.01); *G06T 2207/10116* (2013.01); *H01L 27/14623* (2013.01)

(58) Field of Classification Search
  CPC ....... A61B 6/587; A61B 6/5241; A61B 6/482; A61B 6/4233; A61B 6/58; G06T 5/50; G06T 7/0014; G06T 1/0007; G06T 2207/10116; G06T 7/0017; H01L 27/14661; H01L 27/14634; H01L 27/14623; H01L 27/14658; H01L 27/14663; G01T 1/2018; H04N 5/32
  See application file for complete search history.

(56) References Cited

U.S. PATENT DOCUMENTS

| | | | |
|---|---|---|---|
| 9,588,235 B2 | 3/2017 | Weisfield et al. | |
| 2010/0284628 A1* | 11/2010 | Inuoe | A61B 6/032 382/275 |
| 2017/0112456 A1* | 4/2017 | Ohga | A61B 6/469 |

OTHER PUBLICATIONS

"View Interpolation for Image Synthesis" to Chen et al. Apple Computer, Inc. 1993, pp. 270-288 (Year: 1993).*

* cited by examiner

*Primary Examiner* — Mark R Gaworecki
(74) *Attorney, Agent, or Firm* — Su IP Consulting (57) ABSTRACT

An X-ray sensing apparatus includes a first photodiode array for imaging a first area, a second photodiode array for imaging a second area that overlaps a portion of the first area, and a light-blocking layer coupled to the first photodiode array that prevents at least a portion of visible light emitted by a scintillator layer of the X-ray sensing apparatus from reaching the second photodiode array. The light-blocking layer includes a first feature that is imagable by the second photodiode array and indicates a position along a first direction and a second feature that is imagable by the second photodiode array and indicates a position along a second direction that is different than the first direction.

21 Claims, 10 Drawing Sheets

MISALIGNMENT COMPENSATION IN DUAL X-RAY IMAGER

BACKGROUND

Unless otherwise indicated herein, the approaches described in this section are not prior art to the claims in this application and are not admitted to be prior art by inclusion in this section.

Digital X-ray imaging has multiple advantages over traditional film-based techniques. By bypassing chemical processing, digital X-ray imaging is more time efficient, provides digital images for immediate image preview, facilitates image enhancement, and generally requires less radiation to produce an image of similar contrast. As a result, digital X-ray imaging is now used in many applications, including medical diagnostics, veterinary care, dental imaging, industrial inspection, and security.

Digital X-ray sensors typically include a scintillator material that is excited by incident X-rays and emits light, which is detected by a plurality of photodiodes, such as amorphous silicon photodiodes. Each photodiode generates a signal (e.g., a voltage that is proportional to incident light intensity) for a different pixel of what will eventually become a digital image. To improve performance, digital X-ray sensors have been developed that include a smaller CMOS-(complementary metal-oxide-semiconductor) based photodiode array in addition to the full-sized array of amorphous silicon photodiodes. CMOS-based photodiodes have the advantages of high frame rates, lower noise, higher reliability, reduced image lag, and higher spatial resolution than TFT-(thin-film transistor) based amorphous silicon photodiodes.

CMOS-based photodiode arrays currently available are generally limited in size, for example on the order of a few inches squared. Consequently, rather than replacing TFT-based photodiodes in digital X-ray sensors, CMOS-based photodiode arrays have been incorporated into so-called "hybrid" digital X-ray sensors, which also include a full-sized TFT-based photodiode array. Thus, a portion of the area imaged by such a digital X-ray sensor can be imaged at the higher spatial resolution and frame-rate of the CMOS-based photodiode array, while the entire area imaged by the X-ray sensor is imaged with the conventional photodiode array.

SUMMARY

In accordance with at least some embodiments of the present disclosure, an X-ray sensing apparatus includes a first photodiode array for imaging a first area; a second photodiode array for imaging a second area that overlaps a portion of the first area; and a light-blocking layer coupled to the first photodiode array that prevents at least a portion of visible light emitted by a scintillator layer of the X-ray sensing apparatus from reaching the second photodiode array. The light-blocking layer includes a first feature that is imagable by the second photodiode array and indicates a first position and a second feature that is imagable by the second photodiode array and indicates a second position that is different than the first position.

In accordance with at least some embodiments of the present disclosure, a method in an X-ray sensing apparatus including a first photodiode array that images a first area and a second photodiode array that images a second area overlapping a portion of the first area is described. The method includes with the first photodiode array, generating a first digital image of a first location indicator and a second location indicator; with the second photodiode array, generating a second digital image of the first location indicator, the second location indicator, and a light-blocking object that is fixed to the first photodiode array; determining an alignment offset between the first photodiode array and the second photodiode array, based on a location of the first location indicator in the first digital image, a location of the second location indicator in the first digital image, a location of the first location indicator in the second digital image, and a location of the second location indicator in the second digital image; and determining an initial location of the light-blocking object relative to the second photodiode array based on the second digital image.

In accordance with at least some embodiments of the present disclosure, a method in an X-ray sensing apparatus including a photodiode array for imaging an area and a scintillator layer is described. The method includes with the photodiode array, generating a digital image of the area and an object that is fixed to an external housing of the X-ray sensing apparatus and prevents at least a portion of visible light emitted from a scintillator layer included in the X-ray sensing apparatus from reaching the photodiode array, wherein the object is disposed between the scintillator layer and the photodiode array; determining a position of the object relative to the photodiode array based on the digital image; and generating an offset correction for a position of the photodiode array relative to the external housing of the X-ray sensing apparatus based on the position of the opaque object.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

One issue associated with the hybrid digital X-ray sensors described in the background is that alignment of the two photodiode arrays can be problematic. Specifically, for applications in which the higher-resolution images generated by the CMOS photodiode array are overlayed onto or otherwise combined with images generated by the TFT-based photodiode array, alignment between the two arrays should be maintained within one pixel width of the TFT-based photodiode array. However, such pixels are on the order of a few tenths of a millimeter in size, and assembly of two photodiode arrays with such tight tolerances is generally not practicable. In addition, in normal use the relative positions of the two photodiode arrays can shift much more than a few pixel widths due to temperature changes in the X-ray sensor and deflections caused by gravity and/or mechanical impacts or other vibrations experienced by the X-ray sensor. Thus, even when the two photodiode arrays are perfectly aligned during fabrication, subsequent use invariably alters such alignment.

Furthermore, some applications of hybrid digital X-ray sensors rely on precise knowledge of the location of the CMOS photodiode array relative to one or more external surfaces of the X-ray sensor, such as cone-beam computed tomography (CBCT). In CBCT, inaccuracies in the position of the center point of the photodiode array employed to capture images can directly affect final image quality. Thus, when the CMOS photodiode array of a hybrid digital X-ray sensor is employed for CBCT imaging, the small changes described above in the position of the CMOS photodiode array relative to the external housing of the X-ray sensor can cause blurring and other issues.

In light of the above, there is a need in the art for systems and methods that address the above limitations of conventional X-ray sensors.

According to embodiments of the present disclosure, an X-ray detector for a digital X-ray acquisition system includes a first photodiode array for imaging an area and a second photodiode array for imaging a portion of the area and a scintillator positioned between the first and the second photodiode arrays. According to the embodiments, the second photodiode array is also configured to simultaneously image an opaque or at least partially light-blocking object when imaging the portion of the area. The opaque or at least partially light-blocking object, referred to hereinafter as an "opaque object," is opaque to visible light and/or prevents at least a portion of visible light incident thereon from being transmitted from the scintillator to the second photodiode array. The opaque object, such as an edge of a reflector layer, is fixed to the first photodiode array and extends into the imaging area of the second photodiode array. Therefore, the opaque object, or one or more features of the opaque object, can be used as a point or points of reference indicating misalignment caused by relative motion between the first and second diode arrays. Thus, for a digital image that is generated based on signals from the second photodiode array, changes in the relative position of the first and second photodiode array can be readily determined and compensated for, including horizontal, vertical, and/or rotational displacement. As a result, such a digital image can be precisely incorporated into or otherwise combined with a digital image that is generated based on signals from the first photodiode array, even when significant displacement has occurred between the two photodiode arrays. A calibration method that enables the above-described misalignment compensation is also described herein.

Figure 1:
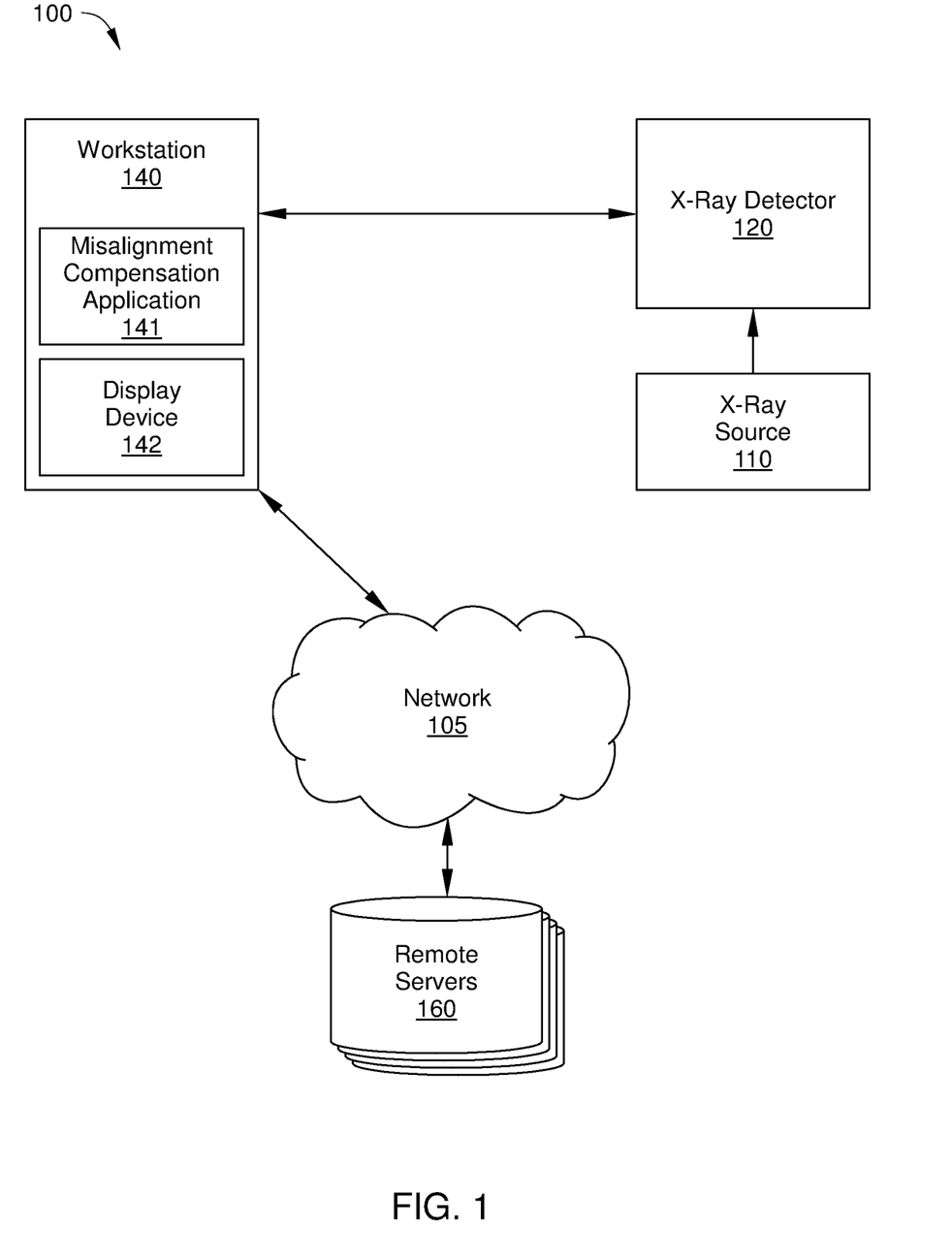
FIG. 1 is a block diagram of a digital X-ray acquisition system, according to one or more embodiments of the present disclosure.

FIG. 1 is a block diagram of a digital X-ray acquisition system 100, according to one or more embodiments of the present disclosure. Digital X-ray acquisition system 100 is a digital X-ray imaging system that is configured to generate raw digital X-ray image data based on incident X-rays, and generate digital images based on the raw digital X-ray image data. As shown, digital X-ray acquisition system 100 includes an X-ray source 110 and an X-ray detector 120 that is connected to a workstation 140, which in turn can connect to remote servers 160 via a network 105. In some embodiments, workstation 140 connects to remote servers 160 via a wireless access point (not shown).

Network 105 may be any technically feasible type of communications network that allows data to be exchanged between digital X-ray acquisition system 100 and remote servers 160. Examples of network 105 may include a wide area network (WAN), a local area network (LAN), a wireless (WiFi) network, and/or the Internet, among others.

X-ray source 110 can include any suitable X-ray source for emitting X-ray photons, such as an X-ray tube (and tube generator). Generally, X-ray source 110 is controlled by workstation 140 or other computing device, via a wired or wireless connection. Specifically, workstation 140 enables selection of X-ray attributes suitable for a specific image acquisition or acquisition session. For example, workstation 140 can control the power supply of X-ray source 110, thereby producing a desired kilovoltage (kVp), current, and duration of exposure. In some embodiments, workstation 140 further includes an alignment compensation application 141 configured to perform some or all of the misalignment compensation operations described herein according to various embodiments. Alternatively or additionally, in some embodiments, some or all of the misalignment compensation operations described herein are performed internally in X-ray detector 120, or in a computing device separate from X-ray detector 120 and workstation 140.

Remote servers 160 are computing devices in which reside information pertinent to operation of X-ray detector 120, such as user data, patient data, previously performed studies, and previously acquired images associated therewith. For example, in some embodiments, remote servers 160 include one or more Digital Image and Communications in Medicine (DICOM) servers, such as a DICOM picture archiving and communication system (PACS) storage server and/or a DICOM PACS review workstation. Such servers provide storage and convenient access to medical images from multiple modalities, thereby enabling a user of X-ray acquisition system 100 to immediately access previously generated medical images and/or studies associated with a particular patient or project.

In some embodiments, factory setup data are stored in remote server 160 that enable misalignment compensation operations to be performed according to various embodiments described herein. For example, the initial location information of an opaque object that is fixed to a first photodiode array in X-ray detector 120 relative to a second photodiode array in X-ray detector 120 can be stored by remote servers 160 rather than on workstation 140.

Workstation 140 may be any technically feasible computing device. For example, in some embodiments, workstation 140 may be desktop or laptop computer that is configured to interact with (e.g., receive output from and provide input to) X-ray detector 120. In other embodiments, workstation 140 may be a suitably programmed mobile computing device, such as a smartphone, a wearable computing device, or an electronic tablet. In either case, workstation 140 is in communication with X-ray detector 120, and is programmed with one or more X-ray detector control applications that enable user interactions with X-ray detector 120, such as configuring X-ray detector 120, operating X-ray detector 120, and performing X-ray detector calibration procedures. As noted above, in some embodiments, one such application is misalignment compensation application 141.

In addition, workstation 140 is typically programmed with an image processing application (not shown) for processing image data received from X-ray detector 120 to generate a digital image. For example, in some embodiments, the image processing application may be configured to convert a digital representation or other image data into a digital image in a specific image file format and/or to modify the resultant digital image. Alternatively or additionally, in some embodiments, the image processing application may provide image processing capability for radiographic (still-picture X-ray) applications and/or fluoroscopic (video X-ray) applications. Alternatively or additionally, in some embodiments, the image processing application can include patient study editing software, image review and/or annotation software, image reprocessing software, and the like. Thus, once a digital representation is received from X-ray detector 120, image generation and post-processing can be performed independently from the operation of X-ray detector 120. In some embodiments, such post-processing includes the incorporation of a digital image generated based on signals from one photodiode array in X-ray detector 120 into a digital image generated based on signals from the other photodiode array in X-ray detector 120, where the two digital images are aligned according to various embodiments described herein.

In some embodiments, workstation 140 may be further configured to query, over a network, a list of patients and studies to be performed, such as a DICOM Modality Worklist Server or other remote server 160; to locally store a list of patients and studies to be performed, similar to a DICOM Modality Worklist Server; to provide a user interface to access a locally stored patient/study list; to maintain a local record of studies performed and images acquired, such as a panel-resident version of a DICOM PACS; to provide a user interface to view and/or review such studies; and to transmit studies performed, including images, directly to one or more of remote servers 160.

X-ray detector 120 is a digital X-ray detector that includes a first photodiode array for imaging a relatively large area (for example, 30 cm×30 cm) and a second photodiode array for imaging a portion of that area (for example, 9 cm×9 cm). Digital signals generated by the first photodiode array can be used to generate a first digital image, and digital signals generated by the second photodiode array can be used to generate a second digital image. According to various embodiments, the second digital image can be aligned with and then incorporated into, or otherwise combined with, the first digital image. Thus, despite changes in relative position between the first photodiode array and the second photodiode array, digital images generated from the first and second photodiode arrays can be precisely aligned. One embodiment of X-ray detector 120 is illustrated in FIG. 2.

Figure 2:
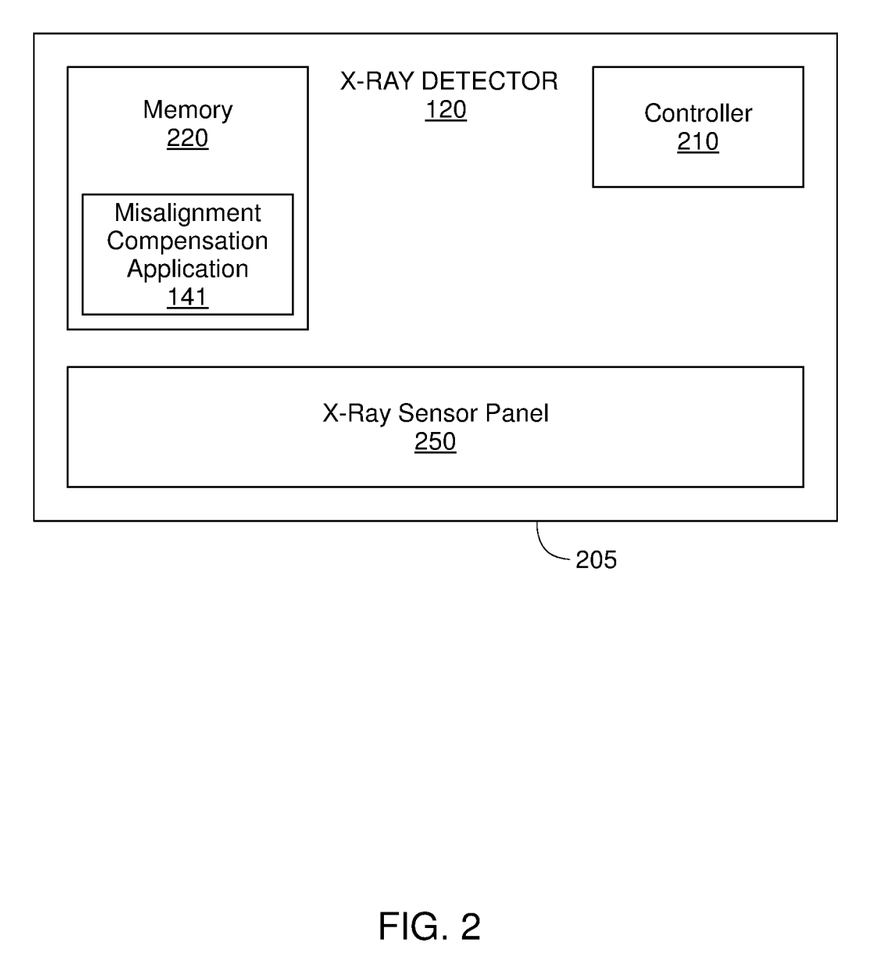
FIG. 2 schematically illustrates an X-ray detector of the digital X-ray acquisition system in FIG. 1, according to one or more embodiments of the present disclosure.

FIG. 2 schematically illustrates X-ray detector 120, according to one or more embodiments of the present disclosure. X-ray detector 120 includes a housing 205, a controller 210, a memory 220, and an X-ray sensor panel 250.

Controller 210 controls the X-ray detector 120 and/or coordinates communication between X-ray detector 120 and workstation 140, and is communicatively coupled to memory 220 and/or a non-volatile data storage medium such as a solid-state drive (SSD). Controller 210 may be any suitable processor implemented as a CPU, an application-specific integrated circuit (ASIC), a field programmable gate array (FPGA), any other type of processing unit, or a combination of different processing units. In general, processing unit 220 may be any technically feasible hardware unit capable of processing data and/or executing software applications residing in memory 220, including an operating system (OS), and, in some embodiments, misalignment compensation application 141. Controller 210 is configured to read data from and write data to memory 220. Memory 220 may include a random access memory (RAM) module, a flash memory unit, any other type of memory unit, or a combination thereof. Memory 220 may include various software programs that can be executed by controller 210 and application data associated with said software programs and/or may be used for data storage. In the embodiment illustrated in FIG. 2, memory 220 is depicted as a separate device from controller 210, but in other embodiments memory 220 can be included in controller 210.

As a first photodiode array, X-ray sensor panel 250 includes a plate with a matrix or array of pixel detector elements formed thereon that each convert incident light to electrical charge. More specifically, X-ray detector 120 is configured as an indirect flat panel detector with a scintillator material that emits light when excited by incident X-rays, and a plurality of photodiodes that detect the emitted light. Each photodiode generates a signal (e.g., a voltage that is proportional to incident light intensity) for a different pixel of what will eventually become a digital image. Controller 210 then interprets each of these voltages and assigns a value to each that is proportional to the voltage. In addition, X-ray sensor panel 250 includes a second photodiode array that is configured to image a portion of the area imaged by the first photodiode array. In some embodiments, the second photodiode array is a different type of photodiode array than the first photodiode array, such as an active-pixel sensor (APS). For example, the second photodiode array may be a CMOS-based photodiode array, a charge-coupled device (CCD), and the like. One such embodiment of X-ray sensor panel 250 is illustrated in FIG. 3.

Figure 3:
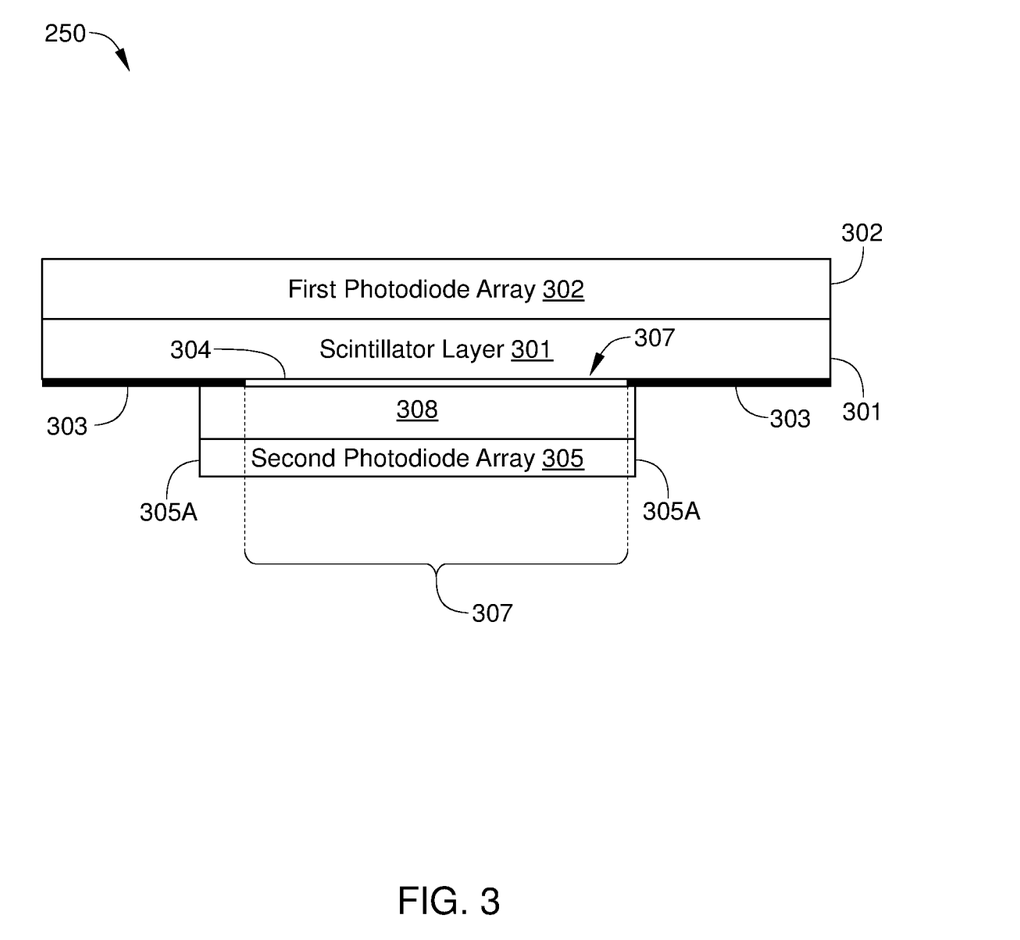
FIG. 3 schematically illustrates a cross-sectional view of an X-ray sensor panel of the X-ray detector in FIG. 2, according to one or more embodiments of the present disclosure.

FIG. 3 schematically illustrates a cross-sectional view of X-ray sensor panel 250, according to one embodiment of the disclosure. X-ray sensor panel 250 includes a scintillator layer 301, a first photodiode array 302, and associated detector circuitry (not shown) formed on a substrate (not shown). Together, scintillator layer 301, first photodiode array 302, and the associated detector circuitry form an X-ray imaging matrix that includes an array of pixel sensors, each pixel containing a photodetector. It is noted that first photodiode array 302 and the associated detector circuitry are generally formed from a plurality of processing layers, and that X-ray sensor panel 250 may include additional material layers not illustrated in FIG. 3.

First photodiode array 302 is a photosensitive element layer that includes a plurality of photosensitive elements, such as photodiodes, photogates, phototransistors, and/or any other suitable circuitry suitable for operation as pixel detector elements in X-ray sensor panel 250. For example, in some embodiments, first photodiode array 302 may include thin-film transistors (TFTs) for reading out the signals from the pixel detector elements. Scintillator material 301 may include one or more material layers including, but no limited to, gadolinium oxisulfide (Gd2O2S:Tb), cadmium tungstate (CdWO4), bismuth germanate (Bi4Ge3O12 or BGO), cesium iodide (CsI), or cesium iodide thallium (CsI:Tl)), among others. In other embodiments, first photodiode array 302 includes a CMOS-based imaging device, CCD-based imaging device, active pixels, passive pixels, and the like, X-ray sensor panel 250 further includes a reflector layer 303 formed on an opposite side of scintillator layer 301 from first photodiode array 302, a dry contact 304 formed on scintillator layer 301, and a second photodiode array 305 coupled to dry contact 304 directly or via a fiber optic plate (FOP) 308. In some embodiments, reflector layer 303 is a metallic layer formed within X-ray sensor panel 250 and, as such, is opaque to visible light, or transmits significantly less visible light than dry contact 304 and FOP 308. Second photodiode array 305 may be a CMOS-based photodiode array, a CCD, or any other suitable active-pixel sensor. Alternatively, second photodiode array 305 may include a TFT-based device, a CCD-based device, or a passive-pixel device. Second photodiode array 305 is disposed as shown on an opposite side of reflector layer 303 from scintillator layer 301, and is optically coupled to scintillator layer 301 by FOP 308. In some embodiments, second photodiode array 305 is fixed to FOP 308 via optical glue. FOP 308 is configured to convey light emitted by scintillator layer 301 to second photodiode array 305 with high efficiency and low distortion. In some embodiments, FOP 308 is an optical device comprised of a bundle of micron-sized optical fibers. Alternatively, any other technically feasible optical device or component can be employed in lieu of FOP 308 to optically couple second photodiode array 305 to scintillator layer 301.

As shown, second photodiode array 305 is substantially aligned with an opening 307 or window formed in reflector layer 303. Furthermore, reflector layer 303 overlaps one or more edges 305A of second photodiode array 305, and therefore extends into the field of view of second photodiode array 305. It is noted that the portion or portions of reflector layer 303 that extend into the field of view of second photodiode array 305 appear as an opaque or significantly less transparent object in any digital image that is generated based on signals from second photodiode array 305. In some embodiments, reflector layer 303 is configured to overlap all edges 305A of second photodiode array 305. One such embodiment is illustrated in FIG. 4.

Figure 4:
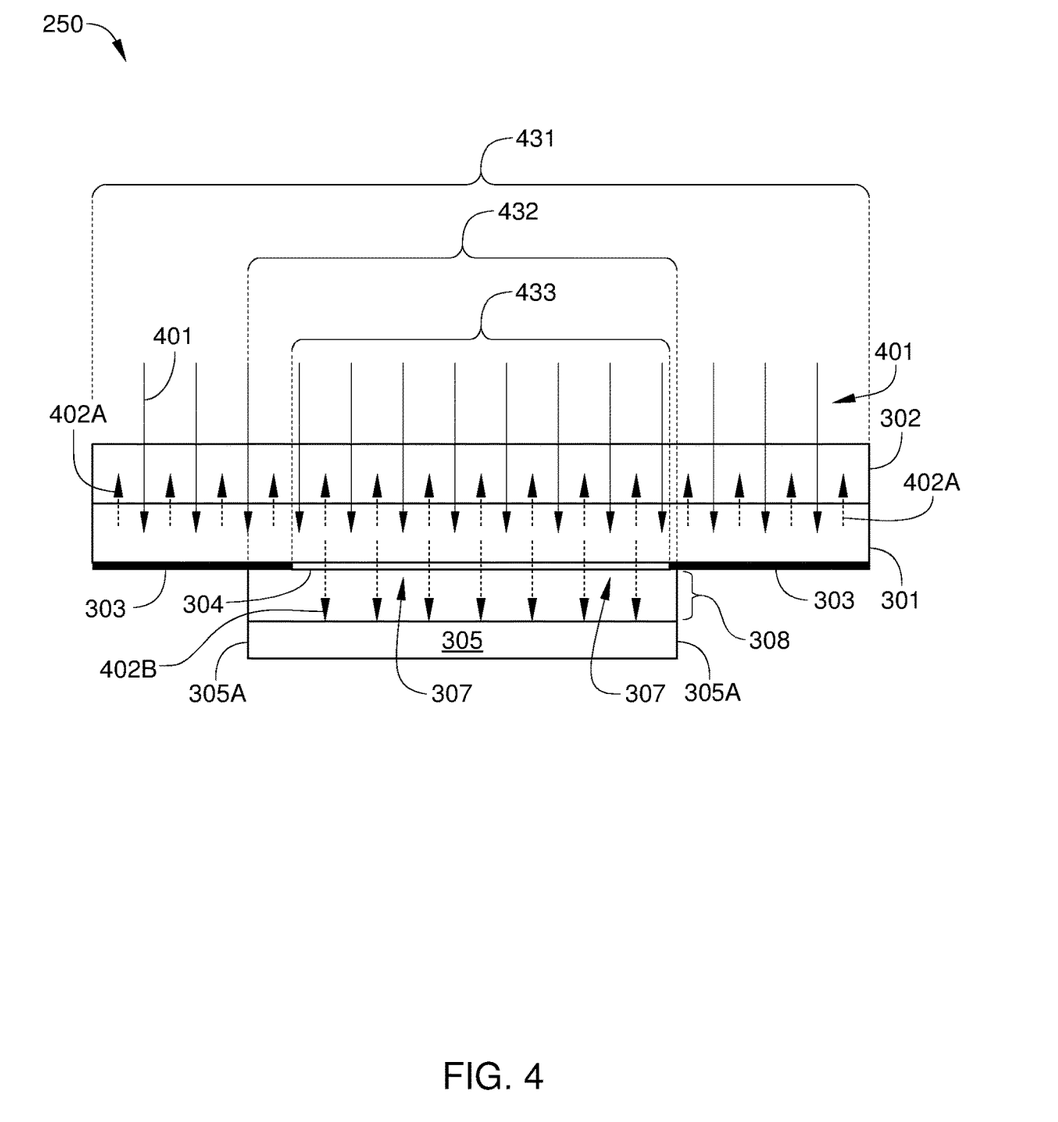
FIG. 4 schematically illustrates a cross-sectional view of the X-ray sensor panel of FIG. 3 in operation, according to one embodiment of the disclosure.

FIG. 4 schematically illustrates a cross-sectional view of X-ray sensor panel 250 in operation, according to one embodiment of the disclosure. As shown, X-rays 401 are incident on X-ray sensor panel 250 and pass through first photodiode array 302 to enter scintillator layer 301. X-rays 401 have passed through a patient or other object of interest after being generated by X-ray source 110. In response, scintillator layer 301 emits visible light 402A toward first photodiode array 302 and visible light 402B toward second photodiode array 305. Each of the pixel detector elements of first photodiode array 302 generates a signal in response to receiving visible light 402A. Taken together, these signals can be employed to generate a digital image of imaging area 431, which is the area through which X-rays 401 pass when incident on first photodiode array 302. Similarly, each of the pixel detector elements of second photodiode array 305 generates a signal in response to receiving visible light 402B through opening 307. Thus, together, these signals can be employed to generate a digital image of imaging area 432, which is the area through which X-rays 401 pass when incident on second photodiode array 305. It is noted that imaging areas 431 and 432 are not necessarily drawn to scale in FIG. 4.

According to various embodiments, one or more portions of reflector layer 303 extend into imaging area 432. Because reflector layer 303 is opaque to visible light or is significantly less transparent to visible light than dry contact 304 and FOP 308, reflector layer 303 is readily imagable by second photodiode array 305. As a result, the one or more portions of reflector layer 303 that extend into imaging area 432 appear as an opaque or substantially opaque object that corresponds in size and location to opening 307. Thus, disregarding the portions of imaging area 432 that are occupied by portions of reflector layer 303, the area that is actually imaged by second photodiode array 305 is effective imaging area 433. One such embodiment is illustrated in FIG. 5.

Figure 5:
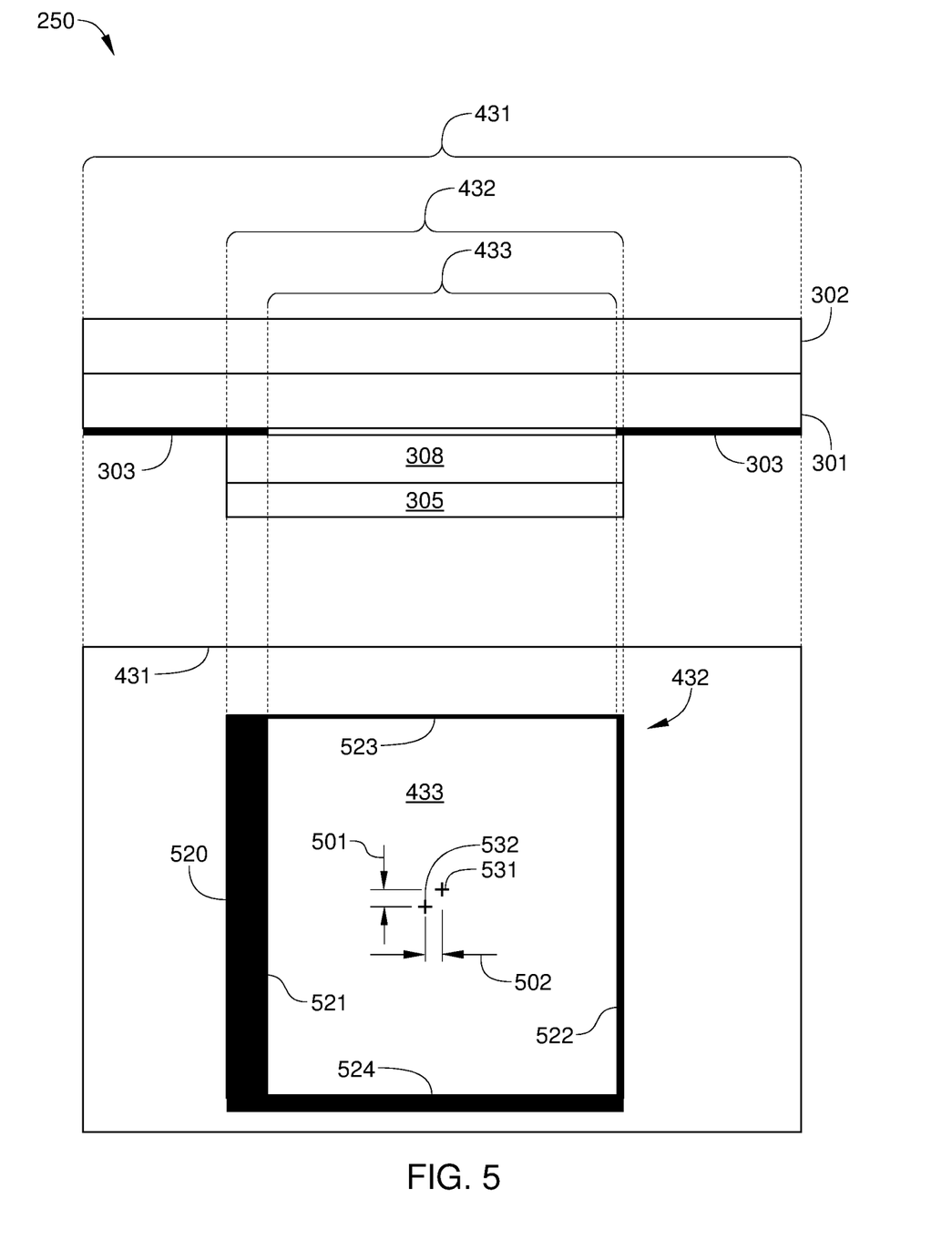
FIG. 5 schematically illustrates a cross-sectional view of the X-ray sensor panel of FIG. 3 and various imaging areas associated with the X-ray sensor panel juxtaposed therewith, according to one embodiment of the disclosure.

FIG. 5 schematically illustrates a cross-sectional view of X-ray sensor panel 250 and imaging areas 431 and 432 juxtaposed therewith, according to one embodiment of the disclosure. Imaging area 431, which is associated with first photodiode array 302, is shown aligned with first photodiode array 302 in FIG. 5, and imaging area 432, which is associated with second photodiode array 305, is shown aligned with second photodiode array 305 in FIG. 5. Also illustrated in FIG. 5 are the portions 520 of reflector layer 303 that extend into imaging area 432 and appear therein as an opaque (or otherwise readily distinguishable) object and are therefore imagable by second photodiode array 305. In the embodiment illustrated in FIG. 5, portions 520 include vertical edges 521 and 522 and horizontal edges 523 and 524. Vertical edges 521 and 522 and horizontal edges 523 and 524 bound effective imaging area 433, which is the area for which a digital X-ray image can be generated based on signals from second photodiode array 305. It is noted that portions 520 exist in imaging area 432 because reflector layer 303 prevents visible light emitted by scintillator layer 303 from reaching certain portions of second photodiode array 305 that correspond portions 520.

Imaging area 432 overlaps a portion of imaging area 431, therefore the area corresponding to imaging area 432 can be imaged by first photodiode array 302, second photodiode array 305, or by both. The exact portion of imaging area 431 that is overlapped by imaging area 432 depends on the position of second photodiode array 305 relative to first photodiode array 302. As described above, the position of second photodiode array 305 relative to first photodiode array 302 can vary over time as a result of deflection of first photodiode array 302 and/or second photodiode array 305 due to gravity, vibration, and/or thermal expansion. Therefore, even when X-ray sensor panel 250 is assembled so that first photodiode array 302 and second photodiode array 305 are in perfect alignment, subsequent relative motion between first photodiode array 302 and second photodiode array 305 generally leads to such alignment not being maintained. One such scenario is illustrated in FIG. 5. Specifically, a center point 531 of imaging area 431 is not aligned with a center point 532 of imaging area 432. Instead, there is a vertical offset 501 between center point 531 and center point 532 and a horizontal offset 502 between center point 531 and center point 532. In some situations, there may also be a rotational offset (not shown), in which imaging area 432 is rotated clockwise or counter-clockwise with respect to imaging area 431.

As second photodiode array 305 moves relative to first photodiode array 302, the values of vertical offset 501, horizontal offset 502, and rotational offset change. Thus, unless vertical offset 501, horizontal offset 502, and any rotational offset between imaging area 431 and 432 are known, a digital image generated based on signals from second photodiode array 305 cannot be incorporated into or otherwise combined with a digital image generated based on signals from first photodiode array 302 without significant positional errors. That is, the digital image generated based on signals from second photodiode array 305 will be offset from the correct location in the digital image generated based on signals from first photodiode array 302, where the offset is equal to vertical offset 501, horizontal offset 502, and/or any rotational offset present.

According to various embodiments, an initial offset between first photodiode array 302 and second photodiode array 305 is determined based on multiple location indicators positioned in imaging area 432. Specifically, the location indicators are imaged by both first photodiode array 302 and second photodiode array 305, and the positions of the location indicators in the resultant digital images can be used to determine an initial value for vertical offset 501, horizontal offset 502, and any rotational offset present between first photodiode array 302 and second photodiode array 305. One such embodiment is illustrated in FIG. 6.

Figure 6:
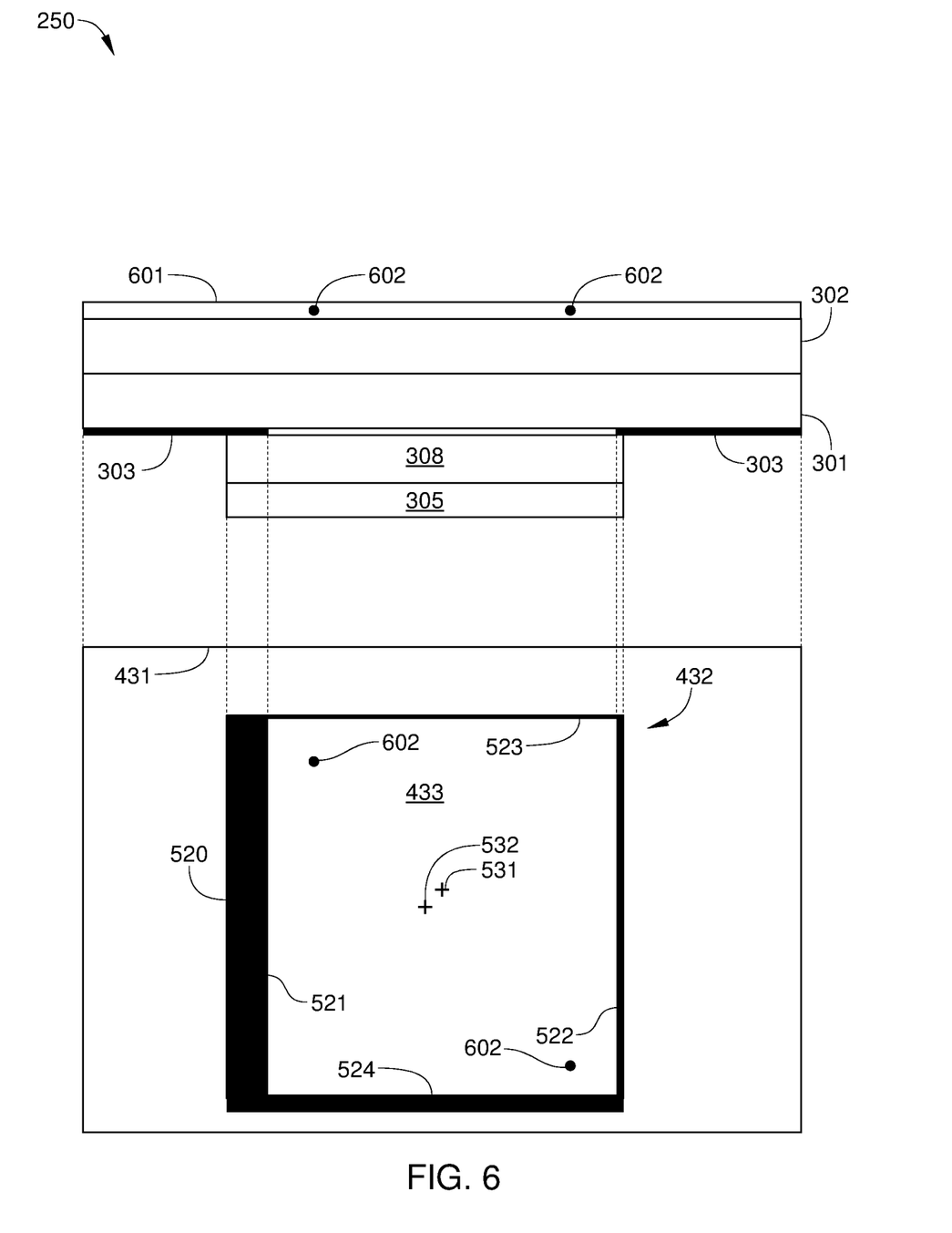
FIG. 6 schematically illustrates a cross-sectional view of the X-ray sensor panel of FIG. 3 and an initial calibration plate, and various imaging areas associated with the X-ray sensor panel juxtaposed therewith, according to one embodiment of the disclosure.

FIG. 6 schematically illustrates a cross-sectional view of X-ray sensor panel 250 and a calibration plate 601 and imaging areas 431 and 432 juxtaposed therewith, according to one embodiment of the disclosure. Calibration plate 601 can be any technically feasible apparatus or material that is transparent to X-rays and can be configured to include two or more location indicators 602 that are opaque to X-rays. For example, in some embodiments, calibration plate 601 includes a plastic sheet or plate with location indicators attached thereto or embedded therein. Location indicators 602 can be any technically feasible device, object or structure that is opaque to X-rays, is significantly less transparent to X-rays than the calibration plate 601, or is significantly more transparent to X-rays than the calibration plate 601. For example, in some embodiments, location indicators 602 may be metallic beads. In some embodiments, location indicators 602 may be holes formed in calibration plate 601 or regions of calibration plate 601 that are more transparent to X-rays than calibration plate 601. In some embodiments, as few as two location indicators 602 are included in calibration plate 601, since at least two reference points are required to determine the two-dimensional offset between first photodiode array 302 and second photodiode array 305. In other embodiments three, four, or more location indicators 602 are included in calibration plate 601. For example, in one such embodiment, a location indicator 602 is disposed proximate each corner region of imaging area 432.

According to some embodiments, during a calibration procedure, calibration plate 601 is positioned on X-ray sensor panel 250 so that location indicators 602 are disposed within imaging area 432, as shown. Consequently, location indicators 602 appear within a digital image of calibration plate 601 that is based on signals from first photodiode array 302 and within a digital image of calibration plate 601 that is based on signals from second photodiode array 305. The locations of location indicators 602 in each of these digital images can be used to determine initial offset values between center point 531 and center point 532. One such embodiment is illustrated in FIGS. 7A and 7B.

Figure 7A:
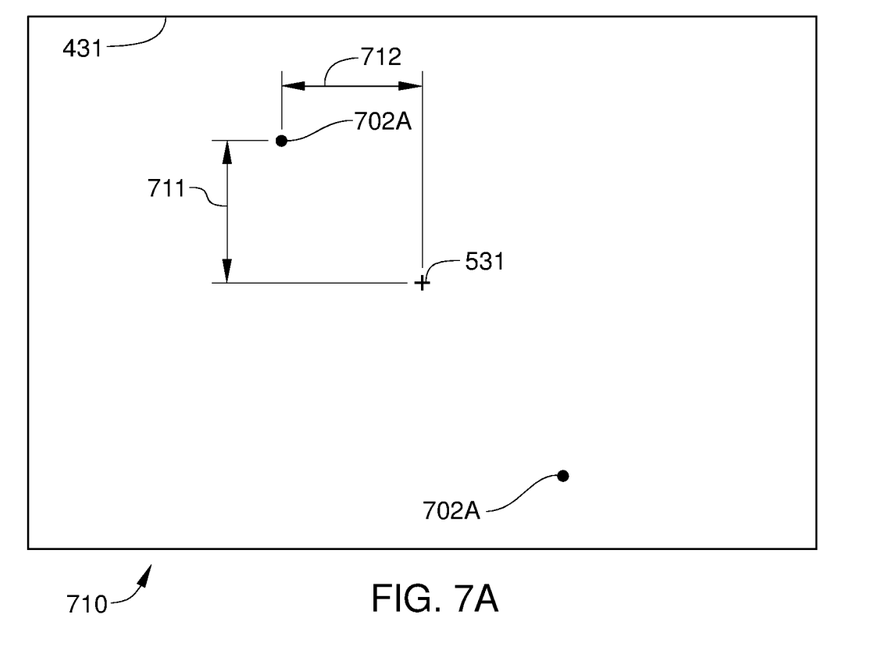
FIG. 7A schematically illustrates a digital image of the initial calibration plate of FIG. 6 that is generated based on signals from a first photodiode array during a calibration procedure, according to one or more embodiments of the present disclosure.

FIG. 7A schematically illustrates a digital image 710 of calibration plate 601 that is generated based on signals from first photodiode array 302 during a calibration procedure, according to one or more embodiments of the present disclosure. Because digital image 710 is based on signals from first photodiode array 302, digital image 710 is an image of imaging area 431, and includes location indicator images 702A of location indicators 602. Location indicator images 702A are generated because location indicators 602 prevent at least a portion of X-rays from reaching an area of scintillator layer 301 that corresponds to the locations of location indicators 602 in imaging area 431. From center point 531 of imaging area 431, each of location indicator images 702A has a respective vertical offset 711 and a respective horizontal offset 712. When digital image 710 is generated during a calibration procedure, vertical offsets 711 and horizontal offsets 712 can be measured, for example in pixels, millimeters, or any other suitable unit of measure.

Figure 7B:
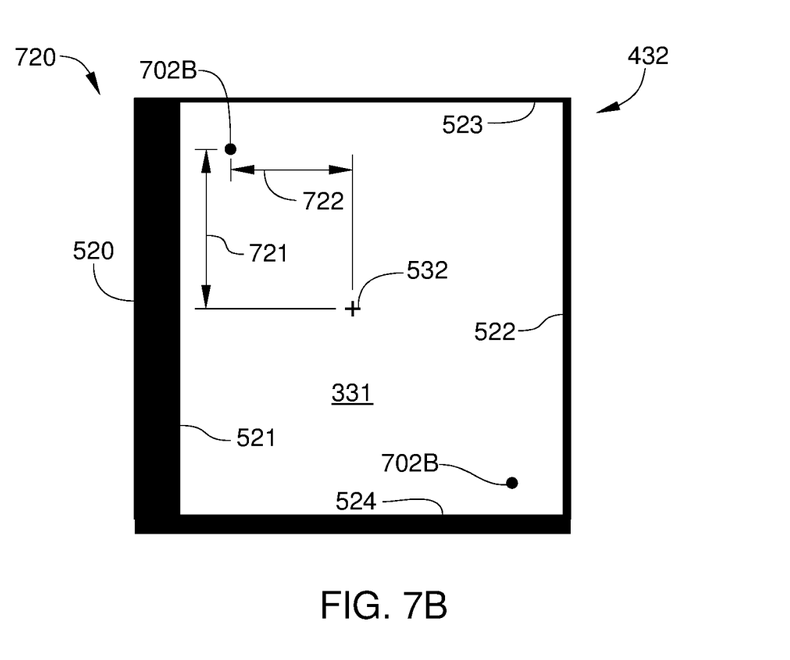
FIG. 7B schematically illustrates a digital image of the initial calibration plate of FIG. 6 that is generated based on signals from a second photodiode array during the same calibration procedure, according to one or more embodiments of the present disclosure.

FIG. 7B schematically illustrates a digital image 720 of calibration plate 601 that is generated based on signals from second photodiode array 305 during the same calibration procedure, according to one or more embodiments of the present disclosure. Because digital image 720 is based on signals from second photodiode array 305, digital image 720 is an image of imaging area 432, and includes location indicator images 702B of location indicators 602. Location indicator images 702B are generated because location indicators 602 prevent at least a portion of X-rays incident on location indicators 602 from reaching a portion of scintillator layer 301 that corresponds to the locations of location indicators 602 in imaging area 432. From center point 532 of imaging area 432, each of location indicator images 702B has a respective vertical offset 721 and a respective horizontal offset 722. When digital image 720 is generated during a calibration procedure, vertical offsets 721 and horizontal offsets 722 can be measured, for example in pixels, millimeters, or any other suitable unit of measure.

According to various embodiments, comparison of the vertical offsets 711 and horizontal offsets 712 of location indicator images 702A with the vertical offsets 721 and horizontal offsets 722 of the corresponding location indicator images 702B can indicate an offset between first photodiode array 302 and second photodiode array 305. For example, when the vertical offsets 711 and horizontal offsets 712 of location indicator images 702A are the same as the corresponding vertical offsets 721 and horizontal offsets 722 of location indicator images 702B, first photodiode array 302 is aligned with second photodiode array 305. That is, center point 531 of imaging area 431 is aligned with center point 532 of imaging area 432. Consequently, a first digital image generated based on signals from second photodiode array 305 can be incorporated into a second digital image generated based on signals from first photodiode array 302 by superimposing center point 532 of the first digital image onto center point 531 of the second digital image. By contrast, in an instance in which the vertical offsets 711 and/or horizontal offsets 712 of location indicator images 702A are not identical to the corresponding vertical offsets 721 and horizontal offsets 722 of location indicator images 702B, first photodiode array 302 is not perfectly aligned with second photodiode array 305. In such an instance, the first digital image is incorporated into the second digital image by positioning the first digital image in the second digital image so that the center point 532 of the first digital image is offset from the center point 531 of the second digital image by the initial offset. Specifically, such an initial offset should be selected to compensate for vertical offset 501 and horizontal offset 502 (shown in FIG. 5) between center point 531 and center point 532. Furthermore, due to rotational offset between digital image 710 and digital image 720, the vertical offset 721 and horizontal offset 722 of one of location indicator images 702B is generally not equal to the vertical offset 721 and horizontal offset 722 of any of the other location indicator images 702B. Thus, vertical offset 721 and horizontal offset 722 for each of location indicator images 702B can also be used to calculate the rotational offset between digital image 710 and digital image 720, using trigonometric calculations well-known in the art.

Figure 8:
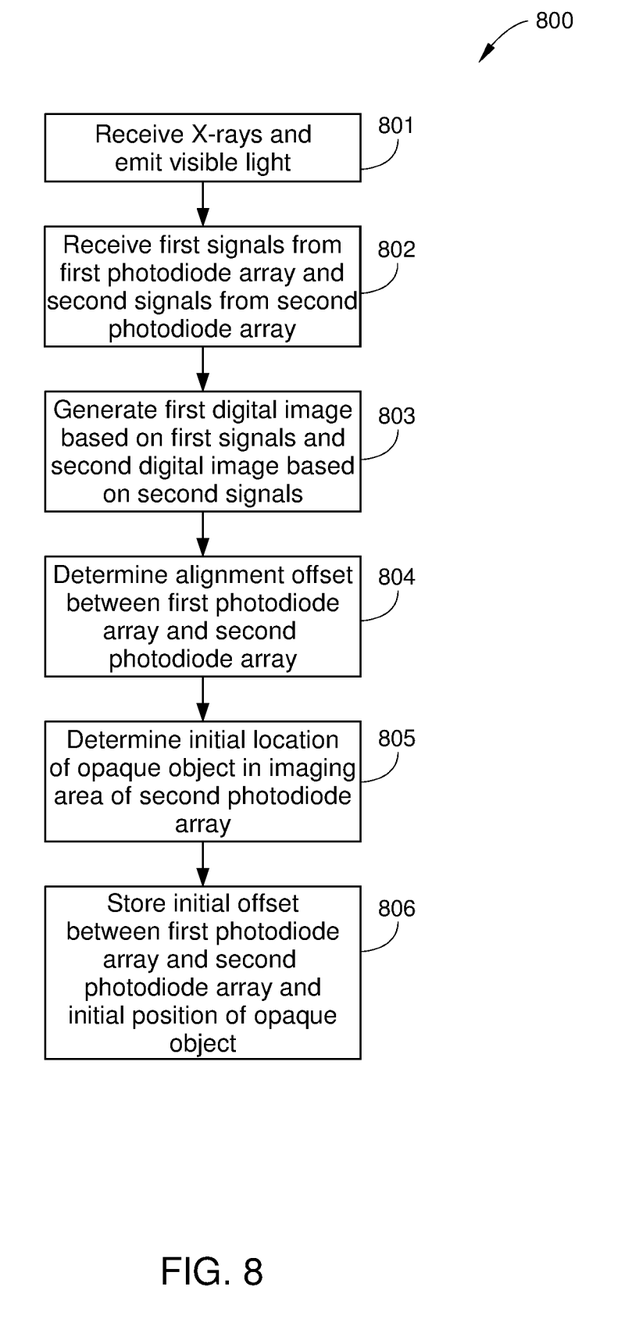
FIG. 8 sets forth a flowchart summarizing an example method for determining an initial offset between a first photodiode array and a second photodiode array in an X-ray sensing apparatus, according to one or more embodiments of the present disclosure.

FIG. 8 sets forth a flowchart summarizing an example method for determining an initial offset between a first photodiode array and a second photodiode array in an X-ray sensing apparatus, according to one or more embodiments of the present disclosure. The method may include one or more operations, functions, or actions as illustrated by one or more of blocks 801-806. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with digital X-ray acquisition system 100 of FIGS. 1-7, persons skilled in the art will understand that any suitably configured digital X-ray system is within the scope of the invention.

In the embodiment described in conjunction with FIG. 8, the control algorithms for the method steps reside in and/or are performed by controller 210. In other embodiments, such control algorithms may reside in and/or be performed by workstation 140, or any other suitable control circuit or computing device. Prior to the method steps, calibration plate 601 is positioned on or in front of X-ray sensor panel 250, so that location indicators 602 are disposed within imaging area 432.

A method 800 begins at step 801, in which X-rays 401 pass through calibration plate 601 and are received by scintillator layer 301, and scintillator layer 301 emits visible light.

In step 802, controller 210 then receives first signals from first photodiode array 302 second signals from second photodiode array 305, which are generated in response to the visible light emitted by first photodiode array 302 and second photodiode array 305.

In step 803, controller 210 causes a first digital image, e.g., digital image 710 in FIG. 7A, to be generated based on the first signals and a second digital image, e.g., digital image 720 in FIG. 7B, to be generated based on the second signals. Digital image 710 includes location indicator images 702A of location indicators 602 and digital image 720 includes location indicator images 702B of location indicators 602. In some embodiments, second digital image also includes an image of an opaque object that is fixed to first photodiode array 302 and extends into imaging area 432

In step 804, controller 210 determines an alignment offset between the first photodiode array and the second photodiode array, for example values for vertical offset 501 and horizontal offset 502 in FIG. 5. Specifically, controller 210 determines such an alignment offset based on the respective locations of location indicator images 702A in digital image 710 and on the respective locations of location indicator images 702B in digital image 720. For example, in some embodiments, for each location indicator image 702A in digital image 710, the vertical offset 711 and horizontal offset 712 from center point 531 of digital image 710 is calculated, measured, or otherwise determined, and for each location indicator image 702B in digital image 720, the vertical offset 721 and horizontal offset 722 from center point 532 of digital image 720 is calculated, measured, or otherwise determined. Then, for each location indicator image 702A in digital image 710, the vertical offset 711 and horizontal offset 712 is compared to the vertical offset 721 and horizontal offset 722 of the corresponding location indicator image 702B in digital image 720, thereby providing a vertical offset 501 and horizontal offset 502 between first photodiode array 302 and second photodiode array 305.

In some embodiments a different datum point in digital images 710 and 720 is employed in lieu of or addition to center point 531 and center point 532. For example a corner point of imaging area 432 may be employed as a datum point in digital image 710, where the corner point is known to correspond to a particular location in imaging area 431 when first photodiode array 302 and second photodiode array 305 are perfectly aligned. In such embodiments, vertical offset 721 and horizontal offset 722 for each location indicator image 702B in digital image 720 are measured with respect to such a datum point rather than with respect to center point 532. Similarly, vertical offset 711 and horizontal offset 712 for each location indicator image 702A in digital image 710 are measured with respect to the corresponding datum point in imaging area 531 rather than with respect to center point 531. Alternatively or additionally, a rotational offset can be calculated between first photodiode array 302 and second photodiode array 305. Specifically, controller 210 can employ any suitable trigonometric algorithm using the vertical offsets 711, horizontal offsets 712, vertical offsets 721, and horizontal offsets 722 to determine such a rotational offset.

In step 805, controller 210 determines an initial location of an opaque object that is fixed to the first photodiode array and is at least partially disposed in imaging area 432. For example, in some embodiments, the opaque object includes the portions 520 of reflector layer 303 that extend into imaging area 432. In some embodiments, the initial location of the opaque object is determined based on a horizontal location and a vertical location, such as a vertical location in imaging area 432 of one of horizontal edges 523 and 524 and a horizontal location in imaging area 432 of vertical edges 521 and 522. One such embodiment is illustrated in FIG. 9.

Figure 9:
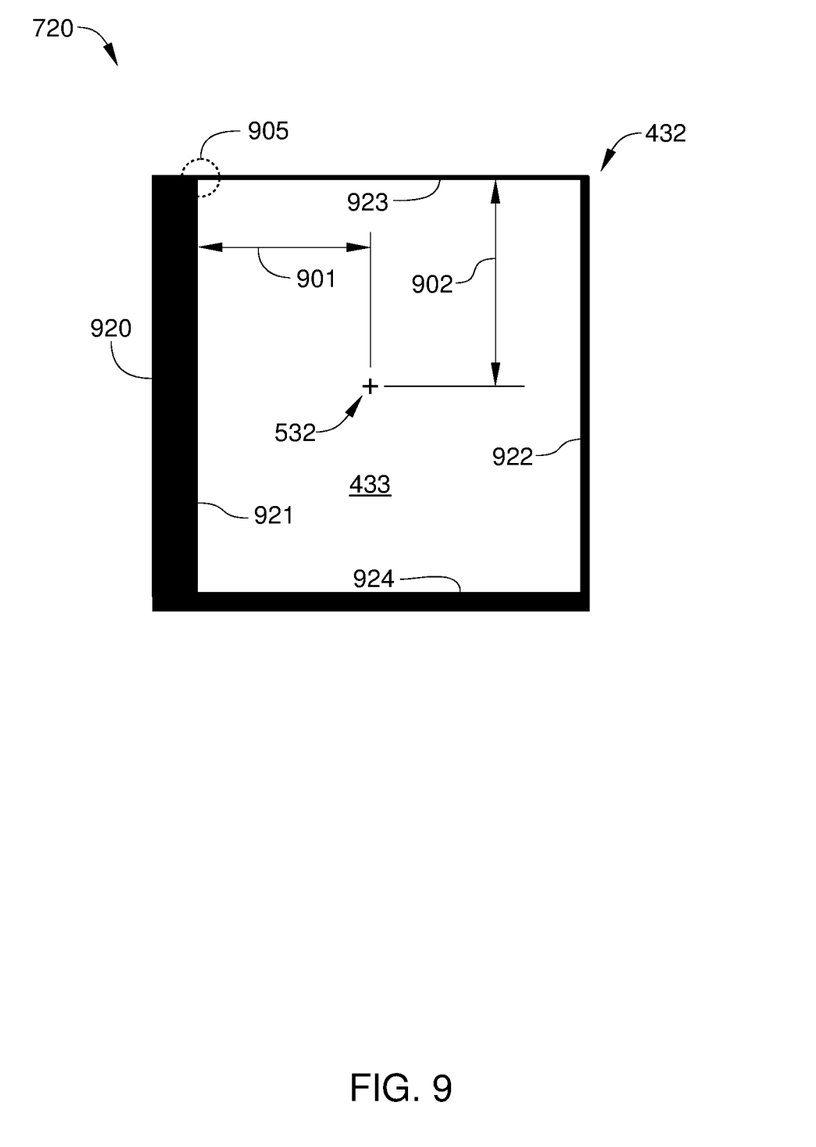
FIG. 9 schematically illustrates an imaging area associated with an X-ray sensor panel and an opaque object disposed in the imaging area, according to one embodiment of the disclosure.

FIG. 9 schematically illustrates imaging area 432 and an opaque object 920 disposed therein, according to one embodiment of the disclosure. As shown, opaque object 920 may include the portions 520 (shown in FIG. 5) of reflector layer 303 that extend into imaging area 432. As such, opaque object 920 includes vertical edges 521 and 522 and horizontal edges 523 and 524, which can be employed by controller 210 as reference points to determine the initial location of opaque object 920 with respect to center point 532. For example, in one embodiment, horizontal distance 901 of vertical edge 921 from center point 532 and vertical distance 902 of horizontal edge 923 from center point 532 can be employed as the initial location of opaque object 920 with respect to center point 532. Alternatively, more than a single horizontal and vertical reference point can be employed by controller 210 to determine the current position of opaque object 920. Alternatively or additionally, any other suitable feature of opaque object 920 can be employed by controller 210 to determine the current position of opaque object 920, such as one or more corner features 905.

Returning to FIG. 8, in step 806, controller 210 stores the initial offset between first photodiode array 302 and second photodiode array 305 and the initial position of opaque object 920 relative to second photodiode array 305. Thus, the initial offset and the initial position can be employed by controller 210 for compensation of subsequent misalignment that occurs between first photodiode array 302 and second photodiode array 305. The initial offset may include vertical and horizontal offset values between first photodiode array 302 and second photodiode array 305 and/or rotational offset values between first photodiode array 302 and second photodiode array 305.

Figure 10:
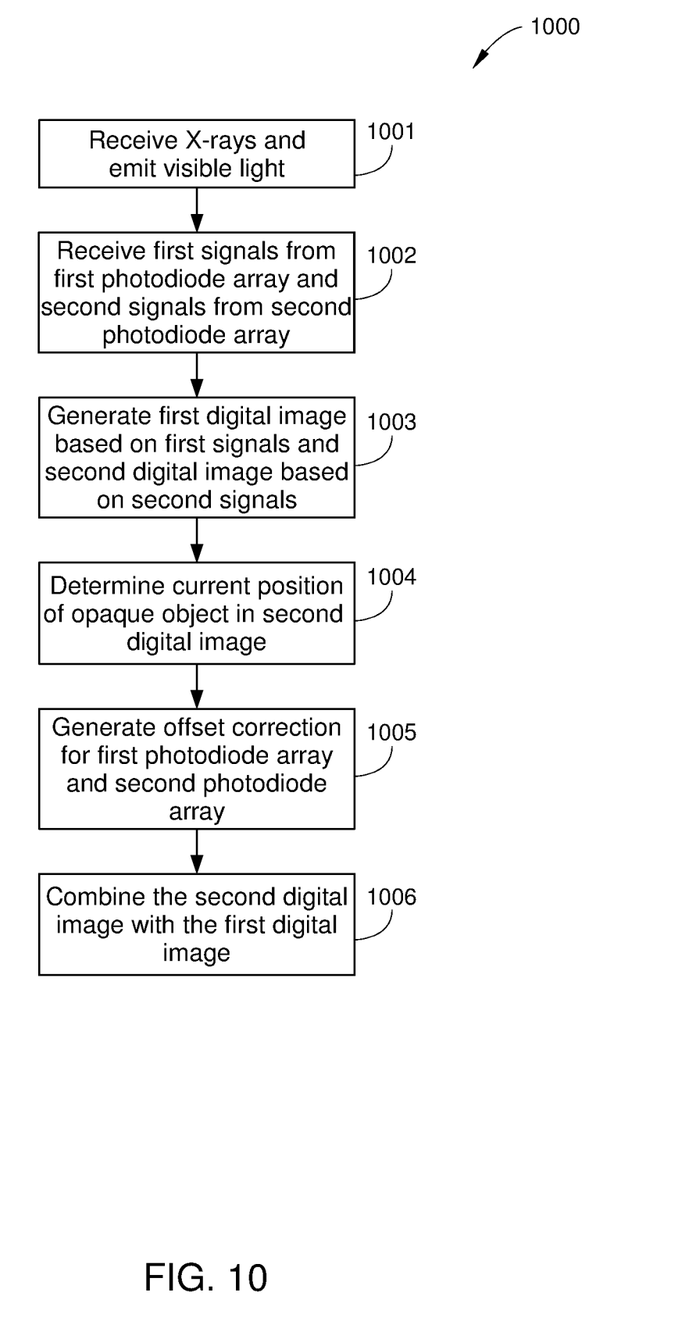
FIG. 10 sets forth a flowchart summarizing an example method for determining and compensating for a current offset between a first photodiode array and a second photodiode array in an X-ray sensing apparatus, according to one or more embodiments of the present disclosure.

FIG. 10 sets forth a flowchart summarizing an example method for determining and compensating for a current offset between a first photodiode array and a second photodiode array in an X-ray sensing apparatus, according to one or more embodiments of the present disclosure. The method may include one or more operations, functions, or actions as illustrated by one or more of blocks 1001-1006. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with digital X-ray acquisition system 100 of FIGS. 1-9, persons skilled in the art will understand that any suitably configured digital X-ray system is within the scope of the invention.

In the embodiment described in conjunction with FIG. 10, the control algorithms for the method steps reside in and/or are performed by controller 210. In other embodiments, such control algorithms may reside in and/or be performed by workstation 140, or any other suitable control circuit or computing device. Prior to the method step, the initial offset between first photodiode array 302 and second photodiode array 305 and the initial position of opaque object 920 relative to second photodiode array 305 are determined, as set forth above in conjunction with FIGS. 8-9.

A method 1000 begins at step 1001, in which X-rays 401 pass through an object of interest and are received by scintillator layer 301, and scintillator layer 301 emits visible light.

In step 1002, controller 210 then receives first signals from first photodiode array 302 and second signals from second photodiode array 305, which are generated in response to the visible light emitted by first photodiode array 302 and second photodiode array 305.

In step 1002, controller 210 then receives first signals from first photodiode array 302 second signals from second photodiode array 305, which are generated in response to the visible light emitted by first photodiode array 302 and second photodiode array 305.

In step 1003, controller 210 causes a first digital image of the object of interest to be generated based on the first signals and a second digital image of the object of interest to be generated based on the second signals. The second digital image includes an image of the opaque object that is fixed to first photodiode array 302 and extends into imaging area 432, such as portions 520 shown in FIG. 5.

In step 1004, controller 210 determines a current position of the image of the opaque object in the second digital image relative to second photodiode array 305 based on the second digital image. For example, controller 210 can determine the current position of the opaque object based on at least one vertical edge and one horizontal edge of the image of the opaque object. Alternatively or additionally, controller 210 determines the current position of the opaque object based on at least one feature included in the image of the opaque object, such as a corner feature or any other feature that inherently indicates a specific horizontal and/or vertical position of the opaque object in imaging area 432.

In step 1005, controller 210 generates an offset correction for the position of first photodiode array 302 relative to second photodiode array 305 based on the current position of the opaque object determined in step 1004 and the initial position of the opaque object determined prior to method 1000. For example, when second photodiode array 305 has shifted N pixels vertically relative to an initial position relative to first photodiode array 302, controller generates an offset correction value that compensates for the shift of N pixels vertically. Thus, in situations in which the second digital image is incorporated into or otherwise combined with the first digital image, the second digital image can be aligned to within one pixel width.

In step 1006, controller 210 combines the second digital image with the first digital image. For example, in some embodiments, a portion of the first digital image is replaced with some or all of the second digital image, which is typically a higher resolution image of imaging area 432. In such embodiments, a datum point of the second digital image, such as center point 532, is shifted by the offset correction generated in step 1005 before replacing portions of the first digital image. In one such embodiment, center point 532 of the second digital image is offset from center point 531 of the first digital, thereby compensating for the relative change in position between first photodiode array 302 and second photodiode array 305 that has taken place since the initial offset therebetween was measured.

In the previously described embodiments, an offset correction is determined and employed to compensate for relative movement between first photodiode array 302 and second photodiode array 305. In other embodiments, such an offset correction can be employed to compensate for relative movement between second photodiode array 305 and one or more surfaces of external housing 205 (shown in FIG. 2). Specifically, in some applications of X-ray detector 120, second photodiode array 305 is employed to generate images that depend on precise knowledge of the location of center point 532 of imaging area 432 relative to one or more reference points or surface of X-ray detector 120. For example in CBCT, an imaging system that includes X-ray detector 120 revolves about an object of interest and dozens or hundreds of images are generated from different imaging locations. A digital volume is then constructed from these images so that three-dimensional anatomical information that can be manipulated and visualized. Even small deflections and translations of second photodiode array 305 can result in an imprecise digital volume that produces blurred images.

In such embodiments, the offset correction that quantifies relative motion between the first photodiode array 302 and the second photodiode array 305 also indicates relative motion between the second photodiode array 305 and external housing 205. This is because first photodiode array 302 is tightly mechanically coupled to external housing 205, i.e., relative motion therebetween is generally very small. Consequently, since there is also very little relative motion possible between reflector layer 303 and first photodiode array 302, a modified embodiment of method 1000 in FIG. 10 can also be employed to determine and compensate for a current offset between second photodiode array 305 and external housing 205. In such a modified embodiment of method 1000, first signals from first photodiode array 302 (received in step 1002) and the first digital image of the object of interest that is generated based on the first signals (generated in step 1002) are not needed to determine the current offset between second photodiode array 305 and external housing 205. In addition, the offset correction determined in step 1005 for the position of first photodiode array 302 relative to second photodiode array 305 (based on the current position of the opaque object) also indicates the current offset between second photodiode array 305 and external housing 205. Thus, in the modified embodiment of method 1000, steps 1002, 1003, and 1005 are modified as described above. It is noted that the modified embodiment of method 1000 can be employed to digitally realign second photodiode array 305 for each image generated by X-ray detector 120. Alternatively, the modified method 1000 can be employed for each Nth image so generated, where N can be any suitable value.

An X-ray detector for a digital X-ray acquisition system includes a first photodiode array for imaging an area and a second photodiode array for imaging a portion of the area. The second photodiode array is also configured to simultaneously image an opaque object when imaging the portion of the area, where the opaque object, positioned between the scintillator and the second photodiode array, is fixed to the first photodiode array and extends into the imaging area of the second photodiode array. The opaque object, or one or more features of the opaque object, can be used as a point or points of reference, indicating misalignment caused by relative motion between the first and second diode arrays. As a result, a digital image generated based on signals from the second photodiode array can be precisely incorporated into or otherwise combined with a digital image that is generated based on signals from the first photodiode array, even when significant displacement has occurred between the two photodiode arrays. A calibration method that enables the above-described misalignment compensation is also described herein.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A method in an X-ray sensing apparatus including a first photodiode array for imaging a first area with a first digital image and a second photodiode array for imaging a second area that overlaps a portion of the first area, the method comprising:
   with the second photodiode array, generating a second digital image of the second area and an object that is fixed to the first photodiode array and prevents at least a portion of visible light emitted from a scintillator layer in the X-ray sensing apparatus from reaching the second photodiode array;
   determining a displacement between a current position of the object relative to the second photodiode array based on the second digital image and an initial position of the object relative to the second photodiode array; and
   generating an offset correction for a position of the first photodiode array relative to the second photodiode array based on the displacement.

2. The method of claim 1, further comprising:
   with the first photodiode array, generating the first digital image of the first area; and
   combining the first digital image and the second digital image.

3. The method of claim 2, wherein combining the portion of the first digital image with the second digital image comprises shifting a datum point of the second digital image by the offset correction.

4. The method of claim 3, wherein shifting the datum point of the second digital image by the offset correction comprises positioning the second digital image so that the datum point of the second digital image is offset from a corresponding datum point of the first digital image by the offset correction.

5. The method of claim 3, wherein the portion of the first digital image corresponds to the portion of the first area that is overlapped by the second area.

6. A non-transitory computer readable medium having instructions stored thereon adapted to perform the method of claim 1.

7. An X-ray sensing apparatus, comprising:
a first photodiode array for imaging a first area area with a first digital image;
a second photodiode array for imaging a second area that overlaps a portion of the first area; and
a light-blocking layer coupled to the first photodiode array that prevents at least a portion of visible light emitted by a scintillator layer of the X-ray sensing apparatus from reaching the second photodiode array, wherein the light-blocking layer includes a first feature that is imagable by the second photodiode array and indicates a first position and a second feature that is imagable by the second photodiode array and indicates a second position that is different than the first position.

8. The X-ray sensing apparatus of claim 7, wherein the first feature indicates the first position along a first direction and the second feature indicates the second position along a second direction.

9. The X-ray sensing apparatus of claim 8, wherein the first feature comprises a first edge of the light-blocking layer and the second feature comprises a second edge of the light-blocking layer.

10. The X-ray sensing apparatus of claim 8, wherein the first feature and the second feature form a corner of the light-blocking layer.

11. The X-ray sensing apparatus of claim 7, wherein the light-blocking layer is configured to overlap all edges of the second photodiode array so that visible light emitted by the scintillator layer is prevented from reaching any edge of the second photodiode array.

12. The X-ray sensing apparatus of claim 7, further comprising a processor that is coupled to the first photodiode array and the second photodiode array and is configured to:
generate a second digital image of the second area and at least a portion of the light-blocking layer based on signals from the second photodiode array;
determine a displacement between a current position of the light-blocking layer relative to the second photodiode array based on the second digital image and an initial position of the object relative to the second photodiode array; and
generate an offset correction for a position of the first photodiode array relative to the second photodiode array based on the displacement.

13. The X-ray sensing apparatus of claim 7, wherein the second area is included entirely within the first area.

14. The X-ray sensing apparatus of claim 7, wherein the light-blocking layer comprises a metal layer formed on a structure that includes the first photodiode array, and the second area corresponds to an opening in the metal layer, wherein the metal layer is disposed between the scintillator layer and the second photodiode array.

15. A method in an X-ray sensing apparatus including a first photodiode array that images a first area and a second photodiode array that images a second area overlapping a portion of the first area, the method comprising:
with the first photodiode array, generating a first digital image of a first location indicator and a second location indicator;
with the second photodiode array, generating a second digital image of the first location indicator and the second location indicator; and
determining an alignment offset between the first photodiode array and the second photodiode array, based on a location of the first location indicator in the first digital image, a location of the second location indicator in the first digital image, a location of the first location indicator in the second digital image, and a location of the second location indicator in the second digital image.

16. The method of claim 15, wherein the alignment offset includes at least one of a horizontal offset value, a vertical offset value, and a rotational offset value.

17. The method of claim 15, wherein the first location indicator comprises a first X-ray-blocking object that prevents at least a portion of X-rays incident on the object from reaching a portion of a scintillator layer that corresponds to a first location in the second area, and wherein the second location indicator comprises a second X-ray-blocking object that prevents at least a portion of X-rays incident on the object from reaching a portion of the scintillator layer that corresponds to a second location in the second area.

18. The method of claim 15, wherein generating the second digital image of the first location indicator and the second location indicator comprises generating an image of a light-blocking object that is fixed to the first photodiode array, and further comprising determining an initial location of the light-blocking object relative to the second photodiode array based on the second digital image.

19. The method of claim 18, wherein determining the initial location of the light-blocking object relative to the second photodiode array based on the second digital image comprises measuring a position of the light-blocking object in the second area.

20. The method of claim 15, wherein:
the first digital image includes one or more additional location indicators;
the second digital image includes the one or more additional location indicators; and
determining the alignment offset between the first photodiode array and the second photodiode array, is further based on a respective location of each of the one or more additional location indicators in the first digital image and on a respective location of each of the one or more additional location indicators in the second digital image.

21. A method in an X-ray sensing apparatus including a photodiode array for imaging an area and a scintillator layer, the method comprising:
with the photodiode array, generating a digital image of the area and an object that is fixed to an external housing of the X-ray sensing apparatus and prevents at least a portion of visible light emitted from a scintillator layer included in the X-ray sensing apparatus from reaching the photodiode array, wherein the object is disposed between the scintillator layer and the photodiode array;
determining a displacement between a current position of the object relative to the photodiode array based on the digital image and an initial position of the object relative to the photodiode array; and
generating an offset correction for a position of the photodiode array relative to the external housing of the X-ray sensing apparatus based on the displacement.

* * * * *